(12) United States Patent
Slaugh et al.

(10) Patent No.: US 6,734,332 B1
(45) Date of Patent: May 11, 2004

(54) PROCESS FOR ENRICHING CIS OR TRANS-ISOMERS IN AN OLEFIN STREAM

(75) Inventors: Lynn Henry Slaugh, Cypress, TX (US); Robert Lawrence Blackbourn, Houston, TX (US); Laura Bridget Palmer, Phoenix, AZ (US); Julie Michelle Freelin, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/325,340

(22) Filed: Dec. 19, 2002

(51) Int. Cl.$^7$ ............................................. C07C 7/152
(52) U.S. Cl. .................... 585/867; 585/864; 585/809
(58) Field of Search ................................. 585/867, 864, 585/804

(56) References Cited

U.S. PATENT DOCUMENTS

| | | | |
|---|---|---|---|
| 4,433,195 A | * 2/1984 | Kulprathipanja | ............ 585/820 |
| 4,946,560 A | 8/1990 | Slaugh et al. | .................. 203/38 |
| 6,184,431 B1 | 2/2001 | Slaugh et al. | ................ 585/867 |
| 6,211,423 B1 | 4/2001 | Slaugh et al. | ................ 585/867 |
| 6,211,432 B1 | 4/2001 | Boudet et al. | ............... 800/278 |
| 6,271,434 B1 | 8/2001 | Slaugh et al. | ................ 585/867 |

OTHER PUBLICATIONS

U.S. patent application Ser. No. 10/325,354, Black et al., filed Dec. 19, 2002.

* cited by examiner

*Primary Examiner*—Thuan D. Dang
(74) *Attorney, Agent, or Firm*—Yukiko Iwata (57) ABSTRACT

An olefin product rich in cis- or trans-isomers can be produced by reacting the mixed olefin feedstock with an linear polyaromatic compound such as anthracene under heat, then separating the unreacted olefin enriched in cis-isomer. The remaining linear unreacted polyaromtic compound and the polyaromatic compound-olefin adduct can be heated to dissociate the adduct to linear polyaromatic compound and olefin stream enriched in trans-isomer.

35 Claims, 3 Drawing Sheets

PROCESS FOR ENRICHING CIS OR TRANS-ISOMERS IN AN OLEFIN STREAM

FIELD OF THE INVENTION

This invention relates to a process for enriching certain isomers in an olefin stream.

BACKGROUND OF THE INVENTION

Many industrial processes produce olefin streams that are mixtures of olefins. Olefins are frequently used in the manufacture of polymers such as polyethylene, as drilling mud additives, or as intermediates for the production of oil additives and detergents. Some industrial processes manufacture olefins streams by oligomerizing ethylene over an alpha olefin catalyst to produce mixtures of olefins having a broad range of carbon numbers. In some applications it will be desirable to obtain olefins enriched in certain isomers for enhanced properties depending on the applications, U.S. Pat. No. 4,946,560 described a process for the separation of internal olefins from alpha olefins by carrying out a Diels-Alder reaction by contacting a feedstock with an adducting compound such as anthracene to form an olefin adduct (Diels-Alder adduct), separating the adduct from the feedstock, dissociating the olefin adduct through heat to produce anthracene and an olefin composition enriched in alpha olefin, and separating out the anthracene from the alpha olefin.

U.S. Pat. No. 6,184,431 describes a process for the separation of alpha and internal olefins from saturated compounds by contacting a feedstock with a linear polyaromatic compound to form a reaction mixture, comprising linear polyaromatic compound-olefin adducts and saturated hydrocarbons, separating the adducts from the saturated hydrocarbons, then dissociating the linear polyaromatic compound-olefin adducts to form linear polyaromatic compounds and an olefin composition.

U.S. Pat. No. 6,271,434 describes a process for the separation of linear alpha olefins from a crude stream containing saturated hydrocarbons, internal olefins, branched olefins, and linear alpha olefins by contacting the feedstock with linear polyaromatic compound to form a reaction mixture comprising linear polyaromatic compound-olefin adducts, separating the adducts from the saturated hydrocarbons and dissociating the adducts to form linear polyaromatic compounds and olefin.

However, it is desirable to obtain a process with economical means to further enrich the desired olefin products.

SUMMARY OF THE INVENTION

There is provided a process for producing an olefin product enriched in trans-isomers from a mixed olefin feedstock comprising cis-isomer olefins and trans-isomer olefins comprising the steps of:

a) contacting the mixed olefin feedstock with a linear polyaromatic compound under conditions effective to form a reaction mixture comprising linear polyaromatic compound-olefin adducts;

b) separating the linear polyaromatic compound-olefin adducts from the unreacted olefins in the reaction mixture to form an adduct stream and an unreacted olefin stream;

c) dissociating the linear polyaromatic compound-olefin adducts in the adduct stream to form linear polyaromatic compounds and an olefin composition enriched in trans-isomer from the mixed olefin feedstock;

d) separating the linear polyaromatic compound formed in step c) from the olefin composition.

Further there is provided a process for producing an olefin product enriched in cis-isomers from a mixed olefin feed stock comprising cis-isomer olefins and trans-isomer olefins comprising the steps of:

a) contacting the mixed olefin feedstock with a linear polyaromatic compound under conditions effective to form a reaction mixture comprising linear polyaromatic compound-olefin adducts;

b) separating the linear polyaromatic compound-olefin adducts from the unreacted olefins in the reaction mixture to form an adduct stream and an unreacted olefin stream enriched in cis-isomers from the mixed olefin feedstock;

c) optionally recovering the olefins from the unreacted olefin stream.

DETAILED DESCRIPTION OF THE INVENTION

This invention relates to a process for enriching cis- and/or trans-isomers of olefin in a mixed olefin stream containing cis-isomer olefins and trans-isomer olefins.

The feed stream to be treated typically comprises olefins, and preferably solvents. Solvents can be any solvent that does not react with the olefins or the linear polyaromatic compound and preferably has appropriate boiling points and miscibility with the olefins and the linear polyaromatic compound such as f or example hydrocarbons such as paraffin.

An olefin means any compound containing at least one carbon-carbon double bond. The olefins may be linear, branched, conjugated, contain multiple double bonds anywhere along the chain, substituted, unsubstituted, contain aryl or alicyclic groups, or contain heteroatoms.

The olefins may contain aryl moieties along with an aliphatic or cycloaliphatic moiety within the same compound, or may consist solely of an aliphatic, cycloaliphatic, or cycloaliphatic with aliphatic moieties on the compound. Preferably, the olefin is an aliphatic compound.

The olefin may be branched or linear. Examples of branching include alkyl, aryl, or alicyclic branches. The number of unsaturation points along the chain is also not limited. The olefin may be a mono-, di-, tri-, etc. unsaturated olefin, optionally conjugated. The olefin may also contain acetylenic unsaturation.

An alpha olefin is an olefin whose double bond is located on both of α and β carbon atoms. An α carbon atom is any terminal carbon atom, regardless of how long the chain is relative to other chain lengths in a molecule. The alpha olefin may be linear or branched. Branches or functional groups may be located on double bond carbon atoms, on carbon atoms adjacent to the double bond carbon atoms, or anywhere else along the carbon backbone. The alpha olefin may also be a poly-ene, wherein two or more points of unsaturation may be located anywhere along the molecule, so long as at least one double bond is in the alpha position.

An internal olefin(s) is an olefin whose double bond is located anywhere along the carbon chain except at any terminal carbon atom. The internal olefin may be linear or branched, and can have cis- and trans-isomers. The location of a branch or substitution on the internal olefin is not limited. Branches or functional groups may be located on the double bond carbon atoms, on carbon atoms adjacent to the double bond carbon atoms, or anywhere else along the carbon backbone. The olefin may also be substituted with chemically reactive functional groups. Examples of chemically reactive functional groups are carboxyl, aldehyde, keto, thio, ether, hydroxyl, and amine. The number of functional groups on a molecule is not limited. The functional groups may be located anywhere along the carbon backbone.

The feedstock can be produced by commercial processes such as the oligomerization of ethylene, optionally followed by isomerization and disproportionation. The feedstock may also be obtained from natural sources such as natural occurring oils and fatty acids and/or synthetic oils and fatty acids. Alternatively, the feedstock may be produced by the Fisher-Tropsch process as decribed in U.S. Pat. Nos. 6,211,432, 6,184,431 and 6,271,434 which disclosures are incorporated by reference herein. A Fisher-Tropsch. process catalytically hydrogenates CO to produce compositions containing aliphatic molecular chains. Other processes for making feedstocks which may contain mixtures of olefins include the dehydrogenation of paraffin, such as those made by the Pacol™ processes of UOP, and the cracking of waxes. The most preferred feedstock is that obtained from a Fisher-Tropsch (FT) synthesis or by oligomerization of ethylene. In order to obtain desired mixed olefin feedstock for the invention, further separation can be conducted such as distillation of certain fractions of olefins, carbon numbers, or boiling point streams, or other separation methods such as described in U.S. Pat. Nos. 6,184,431, 6,211,423, 6,271,434, and 4,946,560 which disclosures are herein incorporated by reference. The preferred amount of olefin present in the mixed olefin stream ranges from 15 wt. % to 100 wt. % . The feedstock may be a processed FT stream which has been fractionated and/or purified by . conventional distillation, extraction, or other separation methods to remove some of the paraffins, high and low molecular weight species, and oxygenates from the crude stream or further separated to provide an stream that is predominantly olefins. It is preferred that the feedstock used in the process of the invention contain am average carbon number ranging from $C_5$–$C_{20}$ and wherein the predominant olefin species in the feedstock is within the range of $C_5$–$C_{20}$, inclusive.

The polyaromatic adducting compound efficiently separates the cis and trans isomers of olefins when the average carbon number of the feedstock and the predominant olefin species is within this range, inclusive, by the formation of the Diels-Alder adduct When the average carbon number of the feedstock exceeds $C_{20}$, the polyaromatic compound-olefin adduct boils at a lower temperature than many of the species in the $C_{20}$ feedstock composition, thereby leaving these high boiling species in the reaction mixture bottoms containing the adduct.

Accordingly, the particular polyaromatic compound and the particular feedstock composition should be so selected that the polyaromatic compound-olefin adduct composition in the reaction mixture boils at a higher temperature than the amount of unreacted paraffin species in the feedstock one desires to separate. Therefore, in this preferred embodiment, the feedstock stream is one which contains an average carbon number in the range from 5 to 20, and more preferably in the range from 6 to 16, and wherein the predominant olefin species is within these ranges, inclusive. These types of streams are generally processed by one of the techniques identified above to substantially remove cuts containing ingredients below or exceeding the range of $C_5$–$C_{20}$.

In the event that one desires to employ a feedstock outside of the range having an average carbon number of from 5 to 20, other separation techniques can be used to separate the adduct from the unreacted reaction mixture, including the selection of higher boiling polyaromatic compounds and/or other separation techniques such as liquid/liquid extraction or crystallization. These techniques, of course, can also be used with feedstocks having average carbon number in the range of 5 to 20, inclusive.

The linear polyaromatic compound is utilized in the instant process to form the adduct with the olefins in the feed stream. As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain so long as at least three fused rings are present in a linear arrangement; as well as those containing a heteroatom which do not interfere in the separation of olefins from saturated hydrocarbons.

The linear polyaromatic compound has a preferential selectivity toward adducting with trans-isomer olefins over cis-isomer olefins. The linear polyaromatic compound of choice is one which has a selectivity for cis-isomer olefins over other olefins greater than 1:1 by mole.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl; etc. The particular substituent size, their number, and their location, should be selected so that they are relatively inert under the reaction conditions and not so large as to block the formation of the Diels-Alder adduct. Suitable substituted linear polyaromatic compounds can be determined by routine experimentation. Examples of suitable linear polyaromatic compounds include 9,10- dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

For enriching the trans-isomer, the process of the instant invention is basically at least a three step process wherein (a) a linear polyaromatic compound is reacted with a feedstock comprising cis- and trans-isomer olefins, to form an adduct of an olefin-linear polyaromatic compound, (b) the adduct is separated from the reaction mixture, typically by flashing or distilling the unreacted olefins enriched in cis-isomers olefins compared to the mixed olefin feedstock and solvents if any at the overhead and recovering the adduct as part of a bottoms stream, (c) the polyaromatic compound-olefin adducts separated in step (b) is dissociated to release the olefins enriched in trans-isomers compared to the mixed olefin feedstock and regenerate the linear polyaromatic compound; and (d) optionally the olefins enriched in trans-isomer olefin is recovered for example, such as distillation. The unreacted and/or dissociated polyaromatic compound can be recycled into the feedstock of step (a).

For enriching the cis-isomer, the process of the instant invention is basically at least a two step process wherein (a) a linear polyaromatic compound is reacted with a feedstock comprising cis- and trans-isomer olefins, to form an adduct of an olefin-linear polyaromatic compound, (b) the adduct is separated from the reaction mixture, typically by flashing or distilling the unreacted olefins enriched in cis-isomers olefins compared to the mixed olefin feedstock and solvents if any at the overhead and recovering the adduct as part of a bottoms stream, (c) optionally the polyaromatic compound-olefin adducts separated in step (b) is dissociated to release the olefins enriched in trans-isomers compared to the mixed olefin feedstock and regenerate the linear polyaromatic compound; and (d) optionally the olefins enriched in cis-isomer olefins is recovered for example, such as distillation. The unreacted and/or dissociated polyaromatic compound can be recycled into the feedstock of step (a).

The Diels-Alder adduct forming reaction is carried out in a conventional fashion and reaction zone. An example of a preferred adduct reaction zone is a plug flow reactor operated in a upflow mode, wherein both the linear polyaromatic compound and the feedstock is mixed and fed into the bottom of the plug flow reactor continuously. The reaction products are continuously withdrawn from the top of the reactor.

Another example of a suitable adduct reaction zone is a continuously stirred tank reactor(s), configured as a single unit, in parallel, or in series, wherein olefin and linear polyaromatic compound are added continuously to a stirred tank(s) to form a liquid reaction mixture, and the reaction mixture is continuously withdrawn from the stirred tank(s).

For lower boiling feedstocks (lighter feedstock), a bubble column may be preferred as the adduct reaction. zone. Alternatively, the reaction may be carried out in a batch reactor.

The adducting reaction is typically carried out at a temperature in the range where the linear polyaromatic compound is in a liquid form. Suitably preferred temperatures are in the range of from about 200°, preferably from about 220° C., most preferably from about 240° C., to about 290° C., preferably to about 280° C., and most preferably to about 265° C. Operating pressures are not critical and set to ensure that none of the olefin stream vaporizes. This pressure will depend on the olefin feedstock used. A typical operating pressure could from about 50 psig (4.5 kg/m$^2$) to about 200 psig (15 kg/m$^2$). The reaction can be carried out in the gas phase under vacuum or liquid phase or mixed gas-liquid phase, depending on the volatility of the feedstock, but generally in the liquid phase.

Stoichiometric ratios or an excess of either olefin or linear polyaromatic compound can be used to form the adducts. The molar ratio of olefin to linear polyaromatic compound is preferably from 0.25:1 up to 10:1. Preferably, a molar excess of linear polyaromatic compound is used to ensure a complete and large recovery of all olefins in the adduction zone, step (a). The residence time is for a time sufficient to adduct the desired amount of linear polyaromatic compound with the olefin. Typical reaction times range from 30 minutes to 4 hours in a batch reaction.

An inert solvent can be utilized to dissolve the feedstock olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. Preferably, the solvent should be a hydrocarbon having 20 carbon atoms or less. The amount of solvent to be employed can vary over a wide range without a deleterious effect on the reaction.

After the linear polyaromatic compound-olefin adduct has been formed, the reaction mixture flows to a separation vessel effective for separating the unreacted olefins and solvents if any from the linear polyaromatic compound-olefin adduct to form a unreacted olefin stream and an adducted stream. Due to the large molecular weight and structural difference between the linear polyaromatic compound-olefin adduct and the unreacted olefin and solvents in the reaction mixture, conventional separation techniques are quite suitable for removing the unreacted olefins. For example, the non-adducted compounds may be removed overhead or in fractions by vacuum or flash distillation of the reaction mixture to leave the linear polyaromatic compound-olefin adduct and unreacted linear polyaromatic compound as a liquid bottoms. The non-adducted compounds which are removed include the unreacted olefins and solvents which did not form an adduct with the linear polyaromatic compound.

Alternatively, the linear polyaromatic compound-olefin adduct is separated by cooling the reaction mixture until the adduct crystallizes out, followed by filtration or centrifugation to remove the unreacted olefin. In most cases, any unreacted linear polyaromatic compound will separate out with the linear polyaromatic compound-olefin adduct in the adducted stream.

The dissociated or released olefins are removed by one or more separation steps such as distillation or crystallization. For example, the released olefins may be removed at the overhead or in fractions by vacuum or flash distillation of the reaction mixture to leave the linear polyaromatic compound-olefin adduct and unreacted or dissociated linear polyaromatic compound as a liquid bottoms.

For recovering the trans-isomer enriched stream, the linear polyaromatic compound-linear alpha olefin adduct is dissociated. The dissociation process can be accomplished by feeding the adducted stream to a dissociation vessel where the adducted stream is heated or pyrolyzed at a temperature effective to dissociate the adduct, typically from about 250° to about 500° C., preferably from about 300° to about 350° C. This pyrolysis frees the olefins from the linear polyaromatic compound. Typically, the majority of the adduct is dissociated. Preferably the adduct is substantially dissociated, i.e., at least 90% by mole, more preferably at least 95% by mole. The remainder of the adduct is removed with the polyaromatic compounds during separation and can be recycled to the adduct reactor. The linear polyaromatic compound is then separated from the resulting mixture by any conventional means, which may occur simultaneously with the pyrolysis operation, such as by vacuum or flash distilling off the olefins along with any impurities at the pyrolysis temperatures, and removing the linear polyaromatic compound as a bottoms from the adduct dissociation zone. Other separation techniques include filtration and centrifugation.

The linear polyaromatic compound may be recycled back to the adduct reaction zone. The separated olefin composition is now enriched in trans-isomer, concentration over that of the feedstock.

The dissociated or released olefins are removed by one or more separation steps such as distillation or crystallization. For example, the released olefins may be removed at the overhead or in fractions by vacuum or flash distillation of the reaction mixture to leave the linear polyaromatic compound-olefin adduct and unreacted or dissociated linear polyaromatic compound as a liquid bottoms.

Each of the olefin composition may be recovered and isolated for use into other applications or as intermediates in other reactive processes.

Figure 1:
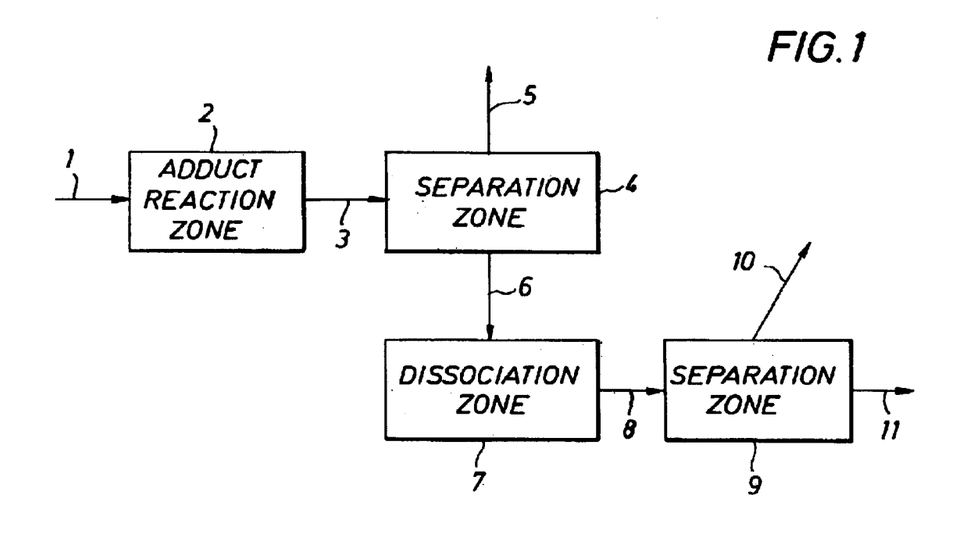
FIG. 1 is a block flow diagram representing an embodiment of the process of providing an olefin stream enriched in the trans-isomer by addcucting, separating, and dissociating.
Figure 2:
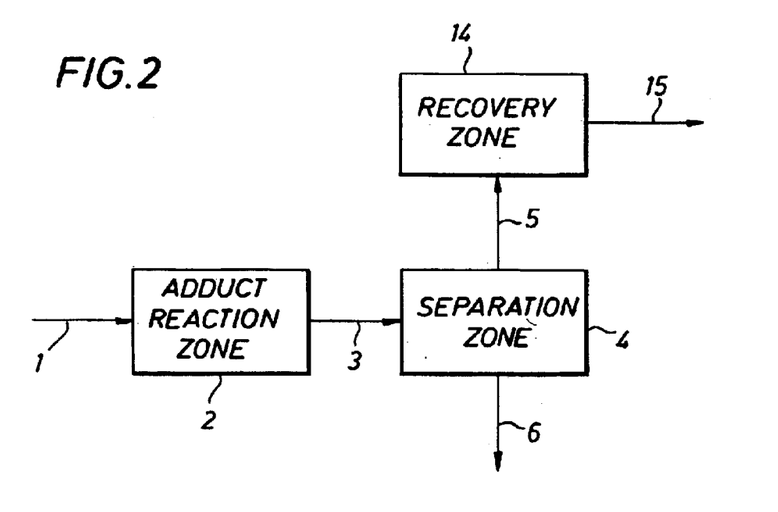
FIG. 2 is a block flow diagram representing an embodiment of the process of providing an olefin stream enriched in the cis-isomer by adducting and separating.

With reference to the Figures, in an embodiment of the invention, the mixed olefin feedstock 1 is provided to an adduct reaction zone 2, whereby the feedstock is contacted with a linear. polyaromatic compound thereby producing a reaction mixture 3 comprising linear polyaromatic compound-olefins adducts, unreacted olefins, and unreacted linear polyaromatic compound if any. The reaction mixture is separated in the separation zone 4 to a unreacted olefin stream 5 comprising unreacted olefins and solvents if any and an adducted stream 6 comprising the linear polyaromatic compound-olefin adducts and unreacted linear polyaromatic compound if any. The adducted stream 6 is provided to the dissociation zone 7. The polyaromatic compound-olefin adduct is completely dissociated (or cracked) in the dissociation zone 7 to form linear polyaromatic compounds and olefins enriched in trans-isomer olefin compared to the mixed olefin feedstock thereby producing a dissociated stream 8. The linear polyaromatic compounds can be separated from the olefins in a separation zone 9 to provide linear polyaromatic compounds stream 10 and olefins stream 11. Optionally the olefins can be recovered from the unreacted olefin stream enrichd in cis-isomer compared to the mixed olefin feedstock, preferably by distllation or flashing to remove at least a portion of the solvents if any, in the recovery zone 14 to provide an olefin product 15 that is enriched in cis-isomer olefins. In a preferred embodiment, both cis-isomer olefin enriched stream and trans-isomer enriched streams are recovered.

Figure 3:
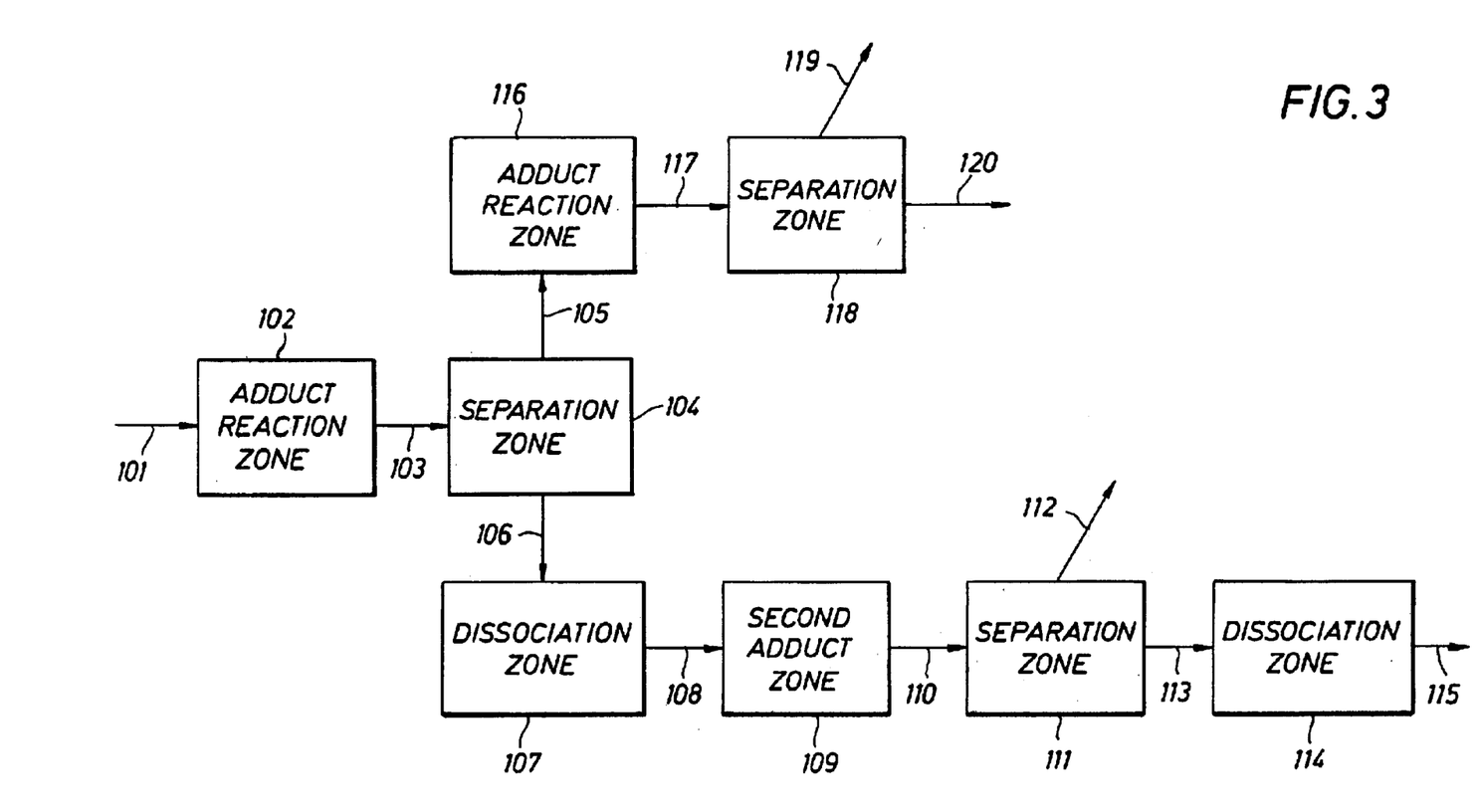
FIG. 3 is a block flow diagram of one embodiment providing an olefin stream enriched in the cis- and/or trans-isomers.

With reference to one of the preferred embodiment FIG. 3, the mixed olefin feedstock 101 is provided to an adduct reaction zone 102, whereby the feedstock is contacted with a linear polyaromatic compound thereby producing a reaction mixture 103 comprising linear polyaromatic compound-olefins adducts, unreacted olefins, and unreacted linear polyaromatic compound if any. The. reaction mixture is separated in the separation zone 104 to a unreacted; olefin stream 105 comprising unreacted olefins and solvents if any and an adducted stream 106 comprising the linear polyaromatic compound-olefin adducts and unreacted linear polyaromatic compound if any. The adducted stream 106 is provided to the dissociation zone 107. The polyaromatic compound-olefin adduct is at least partially, more preferably majority and most preferably completely dissociated (or cracked) in the dissociation zone 107 to form linear polyaromatic compounds and olefins enriched in trans-isomer olefin compared to the mixed olefin feedstock thereby producing a dissociated stream 108. The dissociated stream 108 is provided to a second adduct zone 109, whereby the at least a portion of the dissociated stream 108 is contacted with a linear polyaromatic compound, that may or may not be recycled from the dissociation zone 107 thereby producing a second reaction mixture 110 comprising linear polyaromatic compound-olefins adducts, second unreacted olefins, and unreacted linear polyaromatic compound if any. The second reaction mixture is separated in the separation zone 111 to a second unreacted olefin stream 112 comprising unreacted olefins enriched in cis-isomer olefins compared to the adduct stream and preferably reduced compared with the mixed feed and solvents if any and a second adducted stream 113 comprising the linear polyaromatic compound-olefin adducts and unreacted linear polyaromatic compound if any. The solvents in the second unreacted olefin stream can optionally be removed by convention methods including by distillation or by flashing. The second adducted stream 113 is provided to the dissociation zone 114. The polyaromatic compound-olefin adduct is completely dissociated (or cracked) in the dissociation zone 114 to form linear polyaromatic compounds and olefins enriched in trans-isomer olefin compared to the mixed olefin feedstock and the dissociated stream thereby producing a second dissociated stream 115.

If it is desirable to recover an olefin stream very enriched in cis-isomers, the unreacted olefins from the unreacted olefin stream 105 is provided to a third adduct reaction zone 116, whereby the unreacted olefin is contacted with a linear polyaromatic compound thereby producing a third reaction mixture 117 comprising linear polyaromatic compound-olefins adducts, unreacted olefins, and unreacted linear polyaromatic compound if any. The third reaction mixture is separated in the separation zone 118 to a third unreacted olefin stream 117 comprising unreacted- olefins enrich in the cis-isomer olefins compared to the mixed olefin feedstock and the unreacted stream 105 and solvents if any and an adducted stream 118 comprising the linear polyaromatic compound-olefin adducts and unreacted linear polyaromatic compound if any. In a further preferred embodiment, the adducted stream 118 can be provided to the third dissociation zone 119. The polyaromatic compound-olefin adduct is completely dissociated (or cracked) in the dissociation zone 119 to form linear polyaromatic compounds and olefins enriched in trans-isomer olefin compared to the unreacted stream 105 thereby producing a third dissociated stream 120.

For the purpose of determining whether a species is enriched or reduced by the process, consider the concentration of the species in the feedstock and in the product stream. If the concentration of the species in the feedstock is higher than its concentration in the product, then the process reduces the species. If the concentration of the species in the product stream is higher than its concentration in the feedstock, then the process enriches the species. For the purpose of determining whether a set of species is enriched or reduced by the process, consider the sum of the concentrations of the set of the species in the feedstock and product stream. If the sum of the concentrations of the set of species in the feedstock is higher than the sum of their concentrations in the product, then the process reduces the set of species. If the sum of the concentrations of the set of species in the product stream is higher than the sum of their concentrations in the feedstock, then the process enriches the set of species.

When a species (set of species) is reduced by the process the percentage reduction of the species (set of species) is calculated by subtracting the concentration of the species (sum of concentrations of the set of species) in the product stream from the concentration of the species (sum of concentrations of the set of species) in the feedstock, then dividing this difference by the concentration of the species (sum of concentrations of the set of species) in the feedstock, and then multiplying by 100. When a species (set of species) is enriched by the process the percentage enrichment of the species (set of species) is calculated by subtracting the concentration of the species (sum of concentrations of the set of species) in the feedstock from the concentration of the species (sum of concentrations of the set of species) in the product stream, then dividing this difference by the concentration of the species (sued of concentrations of the set of species) in the feedstock, and then multiplying by 100.

For example, consider that a feedstock contains 35% trans-decene and 5% cis-decene, while the product stream contains 90% trans-decene and 2% cis-decene. Considering only trans-decene, trans-decene is enriched by the process. The percentage enrichment of trans-decene is given as $((90-35)/35) \times 100 = 157.1\%$. Considering only cis-decene, cis-decene is reduced by the process. The percentage reduction of cis-decene is given by $((5-2)/5) \times 100 = 60\%$.

Another measure of enrichment or reduction by the process is the enrichment or reduction of a subset of a set of species relative to the set of species. For the purpose of determining whether a subset of set of species is enriched or reduced by the process, consider the sum of concentrations of the subset in the feedstock and in the product stream. If the sum of concentrations of the subset in the feedstock is higher than the sum of concentrations of the subset in the product, then the process reduces the subset of the set of species. If the sum of the concentrations of the subset in the product stream is higher than the sum of the concentrations of the subset in the feedstock, then the process enriches the subset of set of species.

Two measures of reduction or enrichment of a subset of a set of species can be used. For reduction, the first measure is calculated by a two-step procedure.

Divide the sum of the concentrations of the subset in the feedstock by the sum of concentrations of the set of species in the feedstock, then multiply 100. Call this: X%. Divide the sum of the concentrations of the subset in the product stream by the sum of concentrations of the set of species in the product stream, then multiply by 100. Call this Y%. The subset relative to the set is then said to be reduced from X% to Y% where Y is less than X. For reduction, the second measure is derived from the first measure by subtracting Y% from X%, then dividing this difference by X%, then multiplying by 100. This is called the percentage reduction of the subset relative to the set of species. For enrichment, the first measure is calculated by a two-step procedure. Divide the sum of the concentrations of the subset in the feedstock by the sum, of concentrations of the set of species in the feedstock, then multiply by 100. Call this X%. Divide the sum of the concentrations of the subset in the product stream by the sum of concentrations of the set of species in the product stream, then multiply by 100. Call this Y%. The subset relative to the set is then said to be enriched from X% to Y% where Y is greater than X. For enrichment, the second measure is derived from the first measure by subtracting X% from Y%, then dividing this difference by X%, then multiplying by 100. This is called the percentage enrichment of the subset relative to-the set of species.

The process of the invention will enrich the total concentration of either cis-isomers or trans-isomers or olefins compared to their respective concentrations in the feedstock.

In one preferred embodiment, the concentration of cis-isomers is enriched by at least 5% of the total olefin concentration compared to the cis-isomers in the total olefin concentration in the feedstock. In another preferred embodiment, the concentration of trans-isomers is enriched by at least 5% of the total olefin concentration compared to the trans-isomers in the total olefin concentration in the feedstock.

As above, the percentage reduction or enrichment of. branched olefins and internal olefins in the olefin, composition depends upon the amount of linear polyaromatic compound, temperature, and residence time of the feedstock in the adducting reaction zone.

The olefin composition stream of the invention is useful as a component in drilling fluids, to react with elemental sulfur to make sulfurized products as extreme pressure agents in metal working fluids, as a co-monomers for the polymerization of polyethylene, as an intermediate in making polyalpha olefins (PAO) used as a lubricant, as a chlorination feed to make polychlorinated hydrocarbons in PVC applications, to react with hydrogen sulfides to make primary and secondary mercaptans as pharmaceutical intermediates and as additives to modify the properties of rubber, as solvents, and as a precursor for the manufacture of plasticizer alcohols and detergent range alcohols and surfactants, which may be derivatized into detergent range sulfates or alkoxysulfates for laundry liquids and powders, dishwashing powders and liquids, bar soap, shampoo, liquid hand soap, and hard surface cleaners. The invention can also be useful for separating undesirable isomers in oils and fatty acids used in food products.

The ranges and limitations provided in the instant specification and claims are those that are believed to particularly point out and distinctly claim the instant invention. It is, however, understood that other ranges and limitations that perform substantially the same function in substantially the same manner to obtain the same or substantially the same result are intended to be within the scope of the instant invention. The present invention will now be illustrated by means of the following illustrative embodiments and examples that are provided for illustration and are not to be construed as limiting the invention.

EXAMPLE A

The quantity of reactants charged to a 25 mL Parr autoclave are given in Table A. An olefin feedstock (49.9% trans-2-heptene and 50.1% cis-2-heptene) was prepared to ensure the molar ratio of the cis to trans olefin was consistent for all runs. Anthracene and the olefin feedstock were loaded into the autoclave in a dry box under nitrogen. Sufficient octane was added to insure solubility of the reactants under reaction conditions The autoclave was sealed, removed from the dry box and placed in a heating mantle. The reactor was heated to 250° C. for 16 hours, followed by cooling to 20° C. The autoclave contents were stirred during heating. The unreacted olefin and octane were removed from the product mixture by distillation. This distillation resulted in the isolation of a mixture that was enhanced in cis-2-heptene (Table A, "Unreacted Olefins" column). The remaining anthracene and the anthracene-olefin adduct mixture was heated at atmospheric pressure, to 250–260° C. for 1 hour, during which time the adducted olefim dissociated to anthracene and olefin. The product (Table A, "Olefin Product" column) enriched in trans-2-heptene was removed from the anthracene by distillation. A small stream of nitrogen gas was passed through the apparatus during the distillation to facilitate product removal and recovery.

The products were analyzed by gas chromatography. The molar percent of the cis-2-heptene and trans-2-heptene in the products are reported in Table A. These results clearly show that cis-2-heptene can be concentrated in the unreacted olefin fraction and that the trans-2-heptene can be concentrated into the product obtained upon dissociation of olefin-anthracene adduct.

The material remaining in the flask consisted of unreacted anthracene and the anthracene-olefin adduct.

The flask and its contents were then heated to about 250° C. to dissociate the adduct to anthracene and Olefin 1 Product described in Table B below. Olefin 1 Product was separated and isolated from the anthracene by distillation. During the distillation process, nitrogen gas was passed through the flask to facilitate removal and recovery of the olefin as it was liberated from the anthracene-olefin adduct 8.9 g of Olefin 1 Product was recovered and its composition determined by gas chromatographic analysis.

The results show that Unreacted Olefins 1 was enriched in cis-2-nonene from the 22.7% present in the feedstock to 41.2% by the process of the invention.

Olefin Product 1 contained only 8.1% cis-2-nonene compared with 22.7% in the feedstock. On the other hand, trans-2-nonene was enriched to 91.9% in the Olefin Product 1 from 75.6% in the feed (Table B).

To obtain an olefin further enriched in cis-2-nonene, 9.1 g (93 mmoles) of Unreacted Olefins 1 was treated with 11.1 g (62 mmoles) of anathracene, as described above, to form a Diels-Alder adduct with the 2-nonene. By distillation, 4.5

TABLE A

| Run # | Name of Substituted Anthracene | Anthracene Charged (mmole) | Olefin Feedstock Charged (mmole) | Octane Charged (mmole) | Unreacted Olefins Mole % | | Olefin Product Mole % | |
|---|---|---|---|---|---|---|---|---|
| | | | | | cis-2-heptene | trans-2-heptene | cis-2-heptene | trans-2-heptene |
| 1 | anthracene | 3.0 | 1.5 | 1.8 | 70.7% | 29.3% | 22.8% | 77.2% |
| 2 | 9-methyl-anthracene | 3.0 | 1.5 | 1.6 | 68.9% | 31.1% | 12.2% | 87.8% |
| 3 | 2-ethyl-anthracene | 3.0 | 1.5 | 1.5 | 64.5% | 35.5% | 19.2% | 80.8% |
| 4 | 9-cyano-anthracene | 3.0 | 1.5 | 1.5 | 52.6% | 47.4% | 9.9% | 90.1% |
| 5 | 9,10-dimethyl-anthracene | 2.0 | 1.0 | 1.0 | 64.5% | 35.5% | 5.6% | 94.4% |
| 6 | 1-methyl-anthracene | 1.0 | 0.5 | 33.1 | 60.0% | 40.0% | 18.2% | 81.8% |

EXAMPLE B

To further illustrate the concept of the invention, a stream comprised of 75.6% trans-2-nonene and 22.7% cis-2-nonene was used as a feedstock. The results described in this example demonstrate that additional enrichment of either cis or trans olefinic isomers can be achieved by repeating the process of this invention on the products initially obtained by treatment of the feedstock according to this invention.

0.17 moles of anthracene having a 95% purity and 21.3 g of the feedstock were-placed in an autoclave. The total olefin content of the charged feed was about 0.21 moles for an olefin/anthracene molar ratio of 1.2:1. The autoclave was sealed and then purged with nitrogen. The autoclave was heated to 255° C. for 12 hours to form the Diels-Alder adduct between the olefin and the anthracene. The autoclave contents were stirred during heating.

Once the reaction was complete, the autoclave was cooled to 20° C. The product mixture was transferred to a glass flask and the unreacted olefin removed at 150° C. by vacuum distillation as Unreacted Olefins 1. The composition of Unreacted Olefins 1 was determined by gas chromatographic analysis.

g of Unreacted Olefins 2 was recovered and shown to contain 61.4% cis-s-nonene compared with only 22.7% in the feedstock and 41.2% in Unreacted Olefins 1. Thermal dissociation, as described above, of the Diels-Alder adduct remaining after the removal of Unreacted Olefins 2 gave 2.5 g of Olefin Product 2, which was enriched in trans-2-nonene to 82.3% compared with 58.8% in Unreacted Olefins 1 and 75.6% in the starting feedstock.

To obtain an olefin further enriched in trans-2-nonene, 8.9 g (91 mmoles) of Olefin Product 1 treated with 12.6 g (70 mmoles) of the anthracene, as described above, to form a Diels-Alder adduct with the 2-nonene. By distillation, as above, 3.3 g (33 mmoles) of Unreacted Olefins 3 was separated from the crude nonene-anthracene mixture. The remaining nonene-anthracene adduct was thermally dissociated, as described above, and 3.7 g (37 mmoles) of Olefin Product 3 recovered. Olefin Product 3 was further enriched in trans-2-nonene. Olefin Product 3 contained 97.2% trans-2-nonene compared with 75.6% in the original feedstock and 91.9% in Olefin Product 1.

TABLE B

SEPARATION OF CIS-2-NONENE AND TRANS-2-NONENE

| Composition | Weight (mmoles) | cis-2-nonene wt % | trans-2-nonene wt % |
|---|---|---|---|
| Feedstock | 21.3 g (210) | 22.7 | 75.6 |
| Unreacted Olefins 1 | 9.1 g (93) | 41.2 | 58.8 |
| Olefin Product 1 | 8.9 g (91) | 8.1 | 91.9 |
| Unreacted Olefins 2 | 4.5 g (46) | 61.4 | 38.6 |
| Olefin Product 2 | 2.5 g (25) | 17.7 | 82.3 |
| Unreacted Olefins 3 | 3.3 g (33) | 16.2 | 83.8 |
| Olefin Product 3 | 3.7 g (37) | 2.8 | 97.2 |

EXAMPLE C

Separation of CIS and Trans Isomers of Funcionalized Olefins

In order to demonstrate that the cis and trans isomers of functionalized olefins can be separated according to the present invention, two experiments were performed using as model substrate feeds 50:50 mixtures of cis- and trans-3-hexen-1-ol and cis- and trans-2-hexen-1-ol. In each instance, 0.08 moles of anthracene, having a purity of 99%, was placed in a suitable autoclave along with 0.08 moles of the functionalized olefin feed and 10 ml of octane diluent. After purging with nitrogen, the autoclave was heated to 255° C. and the contents stirred for six hours. When cis- and trans-e-hexen-1-ol was the feed, 67.7 of the olefin was converted to the anthracene-olefin Diels-Alder adduct. With cis- and trans-2-hexen-1-ol substrate, 48% of the olefin was converted to the anthracene-olefin adduct.

In each instance, after transferring the crude product mixture to a glass flask, the unreacted functionalized olefin was removed by distillation (Unreacted Olefin, Table C). The residual adduct/anthracene mixture was then heated to 250° C. over a period of 1.5 hours, a stream of nitrogen was passed through the flask to sweep the product olefin (Olefin Product, Table C) into a cold trap as it was formed by dissociation of the anthracene/olefin adduct.

The tabulated results in Table C demonstrate that the cis olefin isomer concentrates in the Unreacted Olefin and that the trans olefin isomer concentrates in the Olefin Product.

TABLE C

| | Feed Composition,[a] mole % | | | | Unreacted Olefin, mole % | | | | Olefin Product, mole % | | | |
|---|---|---|---|---|---|---|---|---|---|---|---|---|
| Run # | cis-3 | trans-3 | cis-2 | trans-2 | cis-3 | trans-3 | cis-2 | trans-2 | cis-3 | trans-3 | cis-2 | trans-2 |
| 7 | 50 | 50 | — | — | 55.4 | 42.0 | 1.1 | 1.5 | 16.4 | 75.3 | 1.6 | 6.7 |
| 8 | — | — | 50 | 50 | 6.2 | 14.8 | 49.0 | 30.0 | 0.2 | 11.8 | 30.5 | 57.5 |

[a]Notations: cis-3 is cis-3-hexen-1-ol, trans-3 is trans-e-hexen-1-ol, cis-2 is cis-2-hexen-1-ol, trans-2 is trans-2-hexen-1-ol

Figure 4:
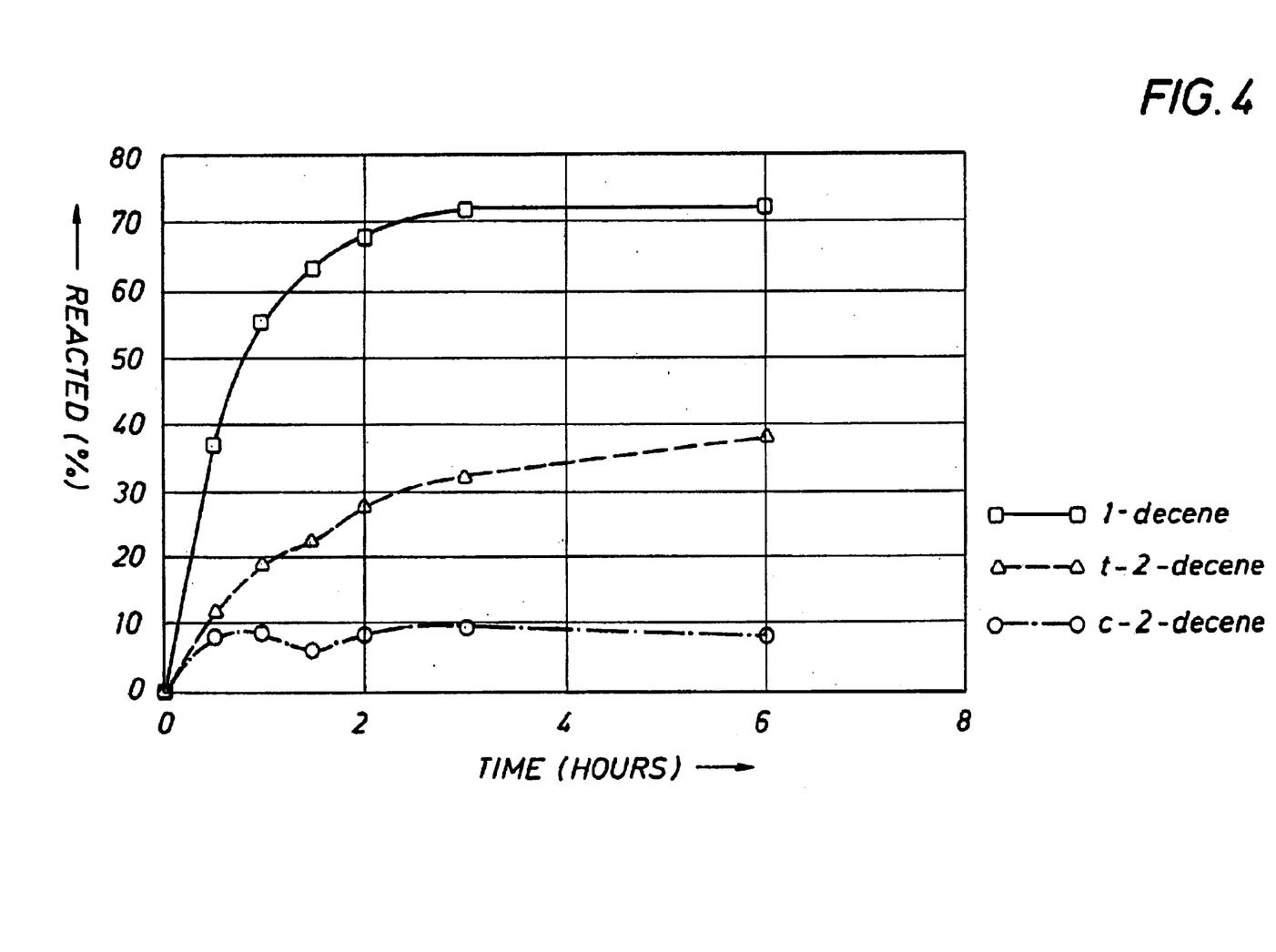
FIG. 4 is a graph of percent olefin isomers reacted versus time for Example D.

EXAMPLE D to further illustrate the invention, a stock solution of approximately 2 g of an olefin feedstock having the following composition was sealed into multiple ampules with anthracene in an anthracene/olefin mole ratio of 1:1.
olefin feedstock: 30% 1-decene, 2.8% 3-decene, 18.8% trans-2-decene, and 48.3% cis-2-decene.
The ampules were then heated to 270° C. for different periods of time, and rapidly quenched in ice water to stop the percent isomers reacted at 270° C. was monitored by gas chromatography over time as shown in FIG. 4.

We claim:

1. A process for producing an olefin product enriched in trans-isomers from a mixed olefin feedstock comprising cis-isomer olefins and trans-isomer olefins comprising the steps of:
   a) contacting the mixed olefin feedstock with a linear polyaromatic compound under conditions effective to form a reaction mixture comprising linear polyaromatic compound-olefin adducts;
   b) separating the linear polyaromatic compound-olefin adducts from the unreacted olefins in the reaction mixture to form an adduct stream and an unreacted olefin stream;
   c) dissociating the linear polyaromatic compound-olefin adducts in the adduct stream to form linear polyaromatic compounds and an olefin composition enriched in trans-isomer compared to the mixed olefin feedstock;
   d) separating the linear polyaromatic compound formed in step c) from the olefin composition.

2. The process of claim 1 wherein the mixed olefin feedstock is contacted with the linear polyaromatic compound in step a) at a temperature in the range from about 200° C. to about 290° C.

3. The process of claim 2 wherein the feedstock is contacted with the linear polyaromatic compound at a temperature ranging from about 220° C. to about 280° C.

4. The process of claim 1 wherein the molar ratio of olefins in the feedstock to linear polyaromatic compounds ranges from greater than 0.25:1 to 10:1.

5. The process of claim 1 wherein the linear polyaromatic compound-olefin adduct is dissociated by heating the linear polyaromatic compound-olefin adduct at a temperature in the range from about 250° C. to about 500° C.

6. The process of claim 5 wherein the linear polyaromatic compound-olefin adduct is heated in the dissociation step to a temperature in the range from about 300° C. to about 350° C.

7. The process of claim 1 wherein the linear polyaromatic compound is separated from the olefin composition by vacuum or flash distillation.

8. The process of claim 1 wherein the separation in step b) is carried out by first cooling followed by filtration or centrifugation.

9. The process of claim 1 wherein the separation in step b) is carried out by distillation.

10. The process of claim 1 wherein the mixed olefin feedstock comprises solvents.

11. The process of claim 10 wherein the separation in step b) is carried out by distillation of the unreacted olefins and solvents.

12. The process of claim 1 wherein the feedstock comprises a stream derived from a Fisher-Tropsch process.

13. The process of claim 10 wherein the feedstock comprises a stream derived from a Fisher-Tropsch process.

14. The process of claim 12 wherein the feedstock comprises from 15 wt. % to 100 wt. % olefins, based on the weight of all ingredients in the feedstock.

15. The process of claim 1 wherein the feedstock has an average carbon number ranging from $C_5$–$C_{20}$ and wherein the predominant olefin species in the feedstock is within the range of $C_5$–$C_{20}$, inclusive.

16. A process for producing an olefin product enriched in cis-isomers from a mixed olefin feed stock comprising cis-isomer olefins and trans-isomer olefins comprising the steps of:
   a) contacting the mixed olefin feedstock with a linear polyaromatic compound under conditions effective to form a reaction mixture comprising linear polyaromatic compound-olefin adducts;
   b) separating the linear polyatomic compound-olefin adducts from the unreacted olefins in the reaction mixture to form an adduct stream and an unreacted olefin stream enriched in cis-isomers compared to the mixed olefin feedstock;
   c) optionally recovering the olefins from the unreacted olefin stream.

17. The process of claim 16 wherein the mixed olefin feedstock is contacted with the linear polyaromatic compound in step a) at a temperature in the range from about 200° C. to about 290° C.

18. The process of claim 17 wherein the feedstock is contacted with the linear polyaromatic compound at a temperature ranging from about 220° C. to about 280° C.

19. The process of claim 16 wherein the molar ratio of olefins in the feedstock to linear polyaromatic compounds ranges from greater than 0.25:1 to 10:1.

20. The process of claim 16 wherein the linear polyaromatic compound-olefin adduct is further dissociated by heating the linear polyaromatic compound-olefin adduct at a temperature in the range from about 250° C. to about 500° C. to form linear polyaromatic compounds and an olefin composition enriched in trans-isomer from the mixed olefin feedstock.

21. The process of claim 20 wherein the linear polyaromatic compound-olefin adduct is heated in the dissociation step to a temperature in the range from about 300° C. to about 350° C.

22. The process of claim 16 wherein the linear polyaromatic compound is separated from the olefin composition by vacuum or flash distillation.

23. The process of claim 16 wherein the separation in step b) is carried out by first cooling followed by filtration or centrifugation.

24. The process of claim 16 wherein the separation in step b) is carried out by distillation.

25. The process of claim 16 wherein the mixed olefin feedstock comprises solvents.

26. The process of claim 25 wherein the separation in step b) is carried out by distillation of the unreacted olefins and solvents.

27. The process of claim 16 wherein the feedstock comprises a stream derived from a Fisher-Tropsch process.

28. The process of claim 25 wherein the feedstock comprises a stream derived from a Fisher-Tropsch process.

29. The process of claim 27 wherein the feedstock comprises from 15 wt. % to 100 wt. % olefins, based on the weight of all ingredients in the feedstock.

30. The process of claim 16 wherein the feedstock has an average carbon number ranging from $C_5$–$C_{20}$ and wherein the predominant olefin species in the feedstock is within the range of $C_5$–$C_{20}$, inclusive.

31. The process of claim 16 wherein in step c) the olefin is recovered by distillation.

32. The process of claim 16 wherein the feedstock comprises a naturally occurring oil and/or fatty acid.

33. The process of claim 16 wherein the feedstock comprises a synthetic oil and/or fatty acid.

34. The process of claim 1 wherein the feedstock comprises a naturally occurring oil and/or fatty acid.

35. The process of claim 1 wherein the feedstock comprises a synthetic oil and/or fatty acid.

* * * * *